United States Patent
Jaffe et al.

(10) Patent No.: US 9,642,515 B2
(45) Date of Patent: May 9, 2017

(54) SOLID STATE CONTINUOUS WHITE LIGHT SOURCE

(71) Applicant: Lumencor, Inc., Beaverton, OR (US)

(72) Inventors: Steven M. Jaffe, Portland, OR (US); Claudia B. Jaffe, Portland, OR (US); George S. Tylinski, Portland, OR (US)

(73) Assignee: LUMENCOR, INC., Beaverton, OR (US)

( * ) Notice: Subject to any disclaimer, the term of this patent is extended or adjusted under 35 U.S.C. 154(b) by 0 days.

(21) Appl. No.: 13/741,474

(22) Filed: Jan. 15, 2013

(65) Prior Publication Data

US 2013/0188331 A1    Jul. 25, 2013

Related U.S. Application Data

(60) Provisional application No. 61/589,086, filed on Jan. 20, 2012, provisional application No. 61/644,921, filed on May 9, 2012.

(51) Int. Cl.
*F21S 4/00* (2016.01)
*F21V 21/00* (2006.01)
(Continued)

(52) U.S. Cl.
CPC .......... *A61B 1/0684* (2013.01); *A61B 1/0646* (2013.01); *A61B 1/0669* (2013.01);
(Continued)

(58) Field of Classification Search
CPC ... F21V 9/16; F21V 7/00; F21V 9/083; A61B 1/0646; A61B 1/0669; A61B 1/0684;
(Continued)

(56) References Cited

U.S. PATENT DOCUMENTS

| 1,998,054 A | 4/1935 | McBurney |
| 3,313,337 A | 4/1967 | Bernat |

(Continued)

FOREIGN PATENT DOCUMENTS

| CA | 2 280 398 | 4/2000 |
| EP | 1 426 807 | 12/2003 |

(Continued)

OTHER PUBLICATIONS

International Search Report dated Jun. 3, 2013 for PCT/US2013/029931, 11 pages.

(Continued)

*Primary Examiner* — Jason Moon Han

(74) *Attorney, Agent, or Firm* — Tucker Ellis LLP

(57) ABSTRACT

A solid state illumination system is provided as a replacement for conventional arc light, metal halide and Xenon white-light sources for applications in microscopy, fluorescence microscopy, and endoscopy. The solid state illumination system generates high quality white light output from LED light sources. The white light output is continuous in the visible spectrum from 380 nm to 650 nm and is suitable for imaging all the most common fluorophores and fluorescent proteins. In embodiments, an LED light pipe engine is used to generate a portion of the spectral content of the white light output.

28 Claims, 7 Drawing Sheets

(51) Int. Cl.
| | |
|---|---|
| *A61B 1/06* | (2006.01) |
| *F21V 9/16* | (2006.01) |
| *F21V 9/08* | (2006.01) |
| *F21V 29/00* | (2015.01) |
| *F21V 8/00* | (2006.01) |
| *F21V 7/00* | (2006.01) |
| *F21V 29/02* | (2006.01) |
| *G02B 21/16* | (2006.01) |
| *G02B 27/14* | (2006.01) |
| *G02B 6/42* | (2006.01) |

(52) U.S. Cl.
CPC ............... *F21V 7/00* (2013.01); *F21V 9/083* (2013.01); *F21V 9/16* (2013.01); *F21V 29/02* (2013.01); *F21V 29/20* (2013.01); *G02B 6/0001* (2013.01); *G02B 6/0003* (2013.01); *G02B 6/0006* (2013.01); *G02B 21/16* (2013.01); *G02B 27/141* (2013.01); *G02B 6/4296* (2013.01)

(58) Field of Classification Search
CPC .. G02B 6/0001; G02B 6/0003; G02B 6/0006; G02B 21/16; G02B 27/141
USPC ............ 362/84, 572, 574, 575, 231, 249.02, 362/311.02, 555
See application file for complete search history.

(56) References Cited

U.S. PATENT DOCUMENTS

| | | | |
|---|---|---|---|
| 3,637,285 A | 1/1972 | Stewart |
| 3,759,604 A | 9/1973 | Thelen |
| 3,881,800 A | 5/1975 | Friesem |
| 3,982,151 A | 9/1976 | Ludovici |
| 4,003,080 A | 1/1977 | Maiman |
| 4,298,820 A | 11/1981 | Bongers |
| 4,371,897 A | 2/1983 | Kramer |
| 4,510,555 A | 4/1985 | Mori |
| 4,539,687 A | 9/1985 | Gordon |
| 4,602,281 A | 7/1986 | Nagasaki et al. |
| 4,626,068 A | 12/1986 | Caldwell |
| 4,642,695 A | 2/1987 | Iwasaki |
| 4,644,141 A | 2/1987 | Hagen |
| 4,657,013 A | 4/1987 | Hoerenz et al. |
| 4,695,332 A | 9/1987 | Gordon |
| 4,695,732 A | 9/1987 | Ward |
| 4,695,762 A | 9/1987 | Berkstresser |
| 4,713,577 A | 12/1987 | Gualtieri |
| 4,724,356 A | 2/1988 | Daehler |
| 4,798,994 A | 1/1989 | Rijpers |
| 4,804,850 A | 2/1989 | Norrish et al. |
| 4,852,985 A | 8/1989 | Fujihara et al. |
| 4,937,661 A | 6/1990 | Van der Voort |
| 4,995,043 A | 2/1991 | Kuwata |
| 5,052,016 A | 9/1991 | Mahbobzadeh |
| 5,089,860 A | 2/1992 | Deppe |
| 5,109,463 A | 4/1992 | Lee |
| 5,126,626 A | 6/1992 | Iwasaki |
| 5,128,846 A | 7/1992 | Mills et al. |
| 5,137,598 A | 8/1992 | Thomas |
| 5,193,015 A | 3/1993 | Shanks |
| 5,200,861 A | 4/1993 | Moskovich |
| 5,226,053 A | 7/1993 | Cho |
| 5,231,533 A | 7/1993 | Gonokami |
| 5,233,372 A | 8/1993 | Matsumoto |
| 5,249,195 A | 9/1993 | Feldman |
| 5,285,131 A | 2/1994 | Muller |
| 5,289,018 A | 2/1994 | Okuda |
| 5,312,535 A | 5/1994 | Waska |
| 5,315,128 A | 5/1994 | Hunt |
| 5,332,892 A | 7/1994 | Li et al. |
| 5,345,333 A | 9/1994 | Greenberg |
| 5,363,398 A | 11/1994 | Glass |
| 5,416,342 A | 5/1995 | Edmond et al. |
| 5,416,617 A | 5/1995 | Loiseaux |
| 5,418,584 A | 5/1995 | Larson |
| 5,428,476 A | 6/1995 | Jensen |
| 5,469,018 A | 11/1995 | Jacobsen |
| 5,475,281 A | 12/1995 | Heijboer |
| 5,478,658 A | 12/1995 | Dodabalapur |
| 5,489,771 A | 2/1996 | Beach et al. |
| 5,493,177 A | 2/1996 | Muller |
| 5,500,569 A | 3/1996 | Blomberg |
| 5,542,016 A | 7/1996 | Kaschke |
| 5,616,986 A | 4/1997 | Jacobsen |
| 5,644,676 A | 7/1997 | Blomberg |
| 5,658,976 A | 8/1997 | Carpenter |
| 5,669,692 A | 9/1997 | Thorgersen |
| 5,671,050 A | 9/1997 | De Groot |
| 5,674,698 A | 10/1997 | Zarling |
| 5,690,417 A | 11/1997 | Polidor et al. |
| 5,715,083 A | 2/1998 | Takayama |
| 5,719,391 A | 2/1998 | Kain |
| 5,757,014 A | 5/1998 | Bruno |
| 5,781,338 A | 7/1998 | Kapitza et al. |
| 5,803,579 A | 9/1998 | Turnbull et al. |
| 5,804,919 A | 9/1998 | Jacobsen |
| 5,808,759 A | 9/1998 | Okamori et al. |
| 5,827,438 A | 10/1998 | Blomberg |
| 5,833,827 A | 11/1998 | Anazawa |
| 5,858,562 A | 1/1999 | Utsugi |
| 5,864,426 A | 1/1999 | Songer |
| 5,942,319 A | 8/1999 | Oyama |
| 5,955,839 A | 9/1999 | Jaffe |
| 5,984,861 A | 11/1999 | Crowley |
| 6,110,106 A | 8/2000 | MacKinnon et al. |
| 6,154,282 A | 11/2000 | Lilge et al. |
| 6,198,211 B1 | 3/2001 | Jaffe |
| 6,204,971 B1 | 3/2001 | Morris |
| 6,222,673 B1 | 4/2001 | Austin |
| 6,293,911 B1 | 9/2001 | Imaizumi et al. |
| 6,299,338 B1 | 10/2001 | Levinson |
| 6,304,584 B1 | 10/2001 | Krupke |
| 6,366,383 B1 | 4/2002 | Roeder |
| 6,392,341 B2 | 5/2002 | Jacobsen |
| 6,404,127 B2 | 6/2002 | Jacobsen |
| 6,404,495 B1 | 6/2002 | Melman |
| 6,422,994 B1 | 7/2002 | Kaneko et al. |
| 6,444,476 B1 | 9/2002 | Morgan |
| 6,513,962 B1 | 2/2003 | Mayshack et al. |
| 6,517,213 B1 | 2/2003 | Fujita et al. |
| 6,529,322 B1 | 3/2003 | Jones |
| 6,542,231 B1 | 4/2003 | Garrett |
| 6,544,734 B1 | 4/2003 | Briscoe |
| 6,594,075 B1 | 7/2003 | Kanao et al. |
| 6,608,332 B2 | 8/2003 | Shimizu |
| 6,614,161 B1 | 9/2003 | Jacobsen |
| 6,614,179 B1 | 9/2003 | Shimizu et al. |
| 6,637,905 B1 | 10/2003 | Ng |
| 6,642,652 B2 | 11/2003 | Collins |
| 6,649,432 B1 | 11/2003 | Eilers |
| 6,674,575 B1 | 1/2004 | Tandler et al. |
| 6,680,569 B2 | 1/2004 | Mueller-Mach et al. |
| 6,685,341 B2 | 2/2004 | Ouderkirk et al. |
| 6,690,467 B1 | 2/2004 | Reel |
| 6,717,353 B1 | 4/2004 | Mueller |
| 6,747,710 B2 | 6/2004 | Hall |
| 6,791,259 B1 | 9/2004 | Stokes et al. |
| 6,791,629 B2 | 9/2004 | Moskovich |
| 6,795,239 B2 | 9/2004 | Tandler et al. |
| 6,843,590 B2 | 1/2005 | Jones |
| 6,869,206 B2 | 3/2005 | Zimmerman et al. |
| 6,870,165 B2 | 3/2005 | Amirkhanian |
| 6,926,848 B2 | 8/2005 | Le Mercier |
| 6,958,245 B2 | 10/2005 | Seul et al. |
| 6,960,872 B2 | 11/2005 | Beeson et al. |
| 6,981,970 B2 | 1/2006 | Karni |
| 6,991,358 B2 | 1/2006 | Kokogawa |
| 6,995,355 B2 | 2/2006 | Rains, Jr. et al. |
| 7,009,211 B2 | 3/2006 | Eilers |
| 7,011,421 B2 | 3/2006 | Hulse et al. |
| 7,035,017 B2 | 4/2006 | Tadic-Galeb |

(56) References Cited

U.S. PATENT DOCUMENTS

| | | |
|---|---|---|
| 7,083,610 B1 | 8/2006 | Murray et al. |
| 7,141,801 B2 | 11/2006 | Goodwin |
| 7,153,015 B2 | 12/2006 | Brukilacchio |
| 7,192,161 B1 | 3/2007 | Cleaver et al. |
| 7,205,048 B2 | 4/2007 | Naasani |
| 7,208,007 B2 | 4/2007 | Nightingale et al. |
| 7,211,833 B2 | 5/2007 | Slater, Jr. et al. |
| 7,239,449 B2 | 7/2007 | Leitel et al. |
| 7,300,175 B2 | 11/2007 | Brukilacchio |
| 7,316,497 B2 * | 1/2008 | Rutherford et al. .......... 362/600 |
| 7,384,797 B1 | 6/2008 | Blair |
| 7,416,313 B2 | 8/2008 | Westphal et al. |
| 7,422,356 B2 | 9/2008 | Hama et al. |
| 7,427,146 B2 | 9/2008 | Conner |
| 7,445,340 B2 | 11/2008 | Conner |
| 7,467,885 B2 | 12/2008 | Grotsch et al. |
| 7,488,088 B2 | 2/2009 | Brukilacchio |
| 7,488,101 B2 | 2/2009 | Brukilacchio |
| 7,498,734 B2 | 3/2009 | Suehiro et al. |
| 7,540,616 B2 | 6/2009 | Conner |
| 7,633,093 B2 | 12/2009 | Blonder et al. |
| 7,709,811 B2 | 5/2010 | Conner |
| 7,746,560 B2 * | 6/2010 | Yamazaki ................ 359/634 |
| 7,832,878 B2 | 11/2010 | Brukilacchio |
| 7,837,348 B2 | 11/2010 | Narendran et al. |
| 7,846,391 B2 | 12/2010 | Jaffe et al. |
| 7,854,514 B2 | 12/2010 | Conner |
| 7,857,457 B2 | 12/2010 | Rutherford et al. |
| 7,898,665 B2 | 3/2011 | Brukilacchio et al. |
| 8,029,142 B2 | 10/2011 | Conner |
| 8,098,375 B2 | 1/2012 | Brukilacchio |
| 8,242,462 B2 | 8/2012 | Jaffe et al. |
| 8,258,487 B1 | 9/2012 | Jaffe et al. |
| 8,263,949 B2 | 9/2012 | Jaffe et al. |
| 8,279,442 B2 | 10/2012 | Brukilacchio et al. |
| 8,309,940 B2 | 11/2012 | Jaffe et al. |
| 2001/0055208 A1 | 12/2001 | Kimura |
| 2002/0109844 A1 | 8/2002 | Christel et al. |
| 2002/0127224 A1 | 9/2002 | Chen |
| 2003/0007087 A1 | 1/2003 | Hakamata et al. |
| 2003/0044160 A1 | 3/2003 | Jonese et al. |
| 2003/0095401 A1 | 5/2003 | Hanson et al. |
| 2003/0127609 A1 | 7/2003 | El-Hage et al. |
| 2003/0160151 A1 | 8/2003 | Zarate et al. |
| 2003/0230728 A1 | 12/2003 | Dai |
| 2003/0233138 A1 | 12/2003 | Spooner |
| 2004/0090600 A1 | 5/2004 | Blei |
| 2004/0247861 A1 | 12/2004 | Naasani |
| 2004/0264185 A1 | 12/2004 | Grotsch et al. |
| 2005/0062404 A1 | 3/2005 | Jones et al. |
| 2005/0116635 A1 | 6/2005 | Walson et al. |
| 2005/0146652 A1 | 7/2005 | Yokoyama et al. |
| 2005/0152029 A1 | 7/2005 | Endo |
| 2005/0184651 A1 | 8/2005 | Cheng |
| 2005/0201899 A1 | 9/2005 | Weisbuch |
| 2005/0248839 A1 | 11/2005 | Yamaguchi |
| 2005/0260676 A1 | 11/2005 | Chandler |
| 2005/0263679 A1 | 12/2005 | Fan |
| 2006/0002131 A1 | 1/2006 | Schultz et al. |
| 2006/0030026 A1 | 2/2006 | Garcia |
| 2006/0060872 A1 | 3/2006 | Edmond et al. |
| 2006/0060879 A1 | 3/2006 | Edmond |
| 2006/0114960 A1 | 6/2006 | Snee |
| 2006/0170931 A1 | 8/2006 | Guo |
| 2006/0237658 A1 | 10/2006 | Waluszko |
| 2006/0282137 A1 | 12/2006 | Nightingale et al. |
| 2007/0009210 A1 | 1/2007 | Hulse |
| 2007/0053184 A1 | 3/2007 | Brukilacchio |
| 2007/0053200 A1 | 3/2007 | Brukilacchio |
| 2007/0058389 A1 | 3/2007 | Brukilacchio |
| 2007/0064202 A1 | 3/2007 | Moffat et al. |
| 2007/0086006 A1 | 4/2007 | Ebersole et al. |
| 2007/0126017 A1 | 6/2007 | Krames et al. |
| 2007/0211460 A1 | 9/2007 | Ravkin |
| 2007/0253733 A1 | 11/2007 | Fey |
| 2007/0279914 A1 | 12/2007 | Rutherford et al. |
| 2007/0279915 A1 | 12/2007 | Rutherford et al. |
| 2007/0280622 A1 | 12/2007 | Rutherford et al. |
| 2007/0281322 A1 | 12/2007 | Jaffe et al. |
| 2007/0284513 A1 | 12/2007 | Fan |
| 2007/0297049 A1 | 12/2007 | Schadwinkel et al. |
| 2008/0079910 A1 | 4/2008 | Rutherford et al. |
| 2008/0089089 A1 * | 4/2008 | Hama et al. ................ 362/574 |
| 2008/0106887 A1 * | 5/2008 | Salsbury et al. ............. 362/84 |
| 2008/0224024 A1 | 9/2008 | Ashdown |
| 2008/0291446 A1 | 11/2008 | Smith |
| 2009/0122533 A1 | 5/2009 | Brukilacchio |
| 2009/0196046 A1 | 8/2009 | Rutherford et al. |
| 2009/0201577 A1 | 8/2009 | LaPlante et al. |
| 2009/0268461 A1 | 10/2009 | Deak et al. |
| 2010/0187440 A1 * | 7/2010 | Jaffe et al. ............... 250/459.1 |
| 2010/0188017 A1 | 7/2010 | Brukilacchio |
| 2011/0044858 A1 | 2/2011 | Jaffe et al. |
| 2011/0234782 A1 * | 9/2011 | Ehrhardt et al. ............ 348/68 |
| 2012/0106192 A1 | 5/2012 | Brukilacchio |
| 2012/0181936 A1 | 7/2012 | Jaffe et al. |
| 2012/0181937 A1 | 7/2012 | Jaffe et al. |
| 2012/0238472 A1 | 9/2012 | Jaffe et al. |
| 2012/0252704 A1 | 10/2012 | Jaffe et al. |

FOREIGN PATENT DOCUMENTS

| | | |
|---|---|---|
| GB | 0943756 | 12/1963 |
| GB | 2 000 173 A | 1/1979 |
| JP | 02-804873 | 7/1998 |
| JP | 2005-195485 | 7/2005 |
| JP | 2005-243973 | 9/2005 |
| JP | 2006-049814 | 2/2006 |
| JP | 2007-133435 | 5/2007 |
| JP | 2011041758 | 3/2011 |
| KR | 10-2006-0055934 | 5/2006 |
| KR | 10-2006-0089104 | 8/2006 |
| WO | WO 02/080577 | 10/2002 |
| WO | WO 2004/114053 | 12/2004 |
| WO | WO 2006/067885 | 6/2006 |
| WO | WO 2006/120586 | 11/2006 |

OTHER PUBLICATIONS

International Search Report dated Dec. 31, 2008, Application No. PCT/US2008/072394, 10 pages.

International Search Report for PCT/US2010021843 dated Aug. 19, 2010, 9 pages.

Extended European Search Report for PCT/US2008072394 dated Oct. 7, 2011, 9 pages.

International Search Report dated Jun. 19, 2012 for Application No. PCT/US2011/063030, 11 pages.

Extended European Search Report for PCT/US2007/069490 dated Oct. 26, 2012, 8 pages.

Albrecht, M., et al., "Scintillators and Wavelength Shifters for the Detection of Ionizing Radiation," Astroparticle, Particle and Space Physics, Detectors and Medical Physics Applications, ICATPP-8, M. Barone, et al., Eds, World Scientific, pp. 502-511 (2004).

Da-Lite Screen Company, Inc., www.da-lite.com, 46 pages website downloads as of Oct. 8, 1998.

DDS™ Rear Projection Screens, LORS™ Reflection Screens, © 1998 Physical Optics Corporation, Torrance, CA, 2 pages.

Deck, L., et al., "Two color light-emitting-diode source for high precision phase-shifting interferometry", Optics Letters, vol. 18, No. 22, Nov. 15, 1993, pp. 1899-1901.

Depp, S.W., et al., "Flat Panel Displays," Scientific American, pp. 90-97, Mar. 1993.

Flor-Henry, M., et al., "Use of a Highly Sensitive Two-Dimensional Luminescence Imaging System to Monitor Endogenous Bioluminescence in Plant Leaves," BMC Plant Biology, vol. 4, No. 19, Nov. 2004.

Hamberg, I. and Granqvist, C.G., "Evaporated Sn-doped $In_2O_3$ films: Basic optical properties and applications to energy-efficient windows," Journal of Applied Physics, vol. 60, No. 11, pp. R123-R159, Dec. 1, 1986.

(56) References Cited

OTHER PUBLICATIONS

Handbook of Optics, vol. 1—Fundamentals, Techniques, and Design, Second Edition, Chapter 42: Optical Properties of Films and Coatings, J.A. Dobrowolski, pp. 42.3-42.25, McGraw-Hill, Inc., © 1995.

Haroche, S., et al., "Cavity Quantum Electrodynamics," Scientific American, pp. 54-62, Apr. 1993.

Hecht, Jeff, "Diverse fiberoptic systems require varied sources," Laser Focus World, vol. 36, No. 1, pp. 155-161, Jan. 2000.

Hemingway, D.J. and Lissberger, P.H., "Effective Refractive Indices of Metal-Dielectric Interference Filters," Applied Optics, vol. 6, No. 3, pp. 471-476, Mar. 1967.

Hinds, E.A., "Spectroscopy of Atoms in a Micron-Sized Cavity," (date and periodical title unknown), pp. 18-19.

Holloway, R.J. and Lissberger, P.H., "The Design and Preparation of Induced Transmission Filters," Applied Optics, vol. 8, No. 3, pp. 653-660, Mar. 1969.

Huo, D.T.C., et al., "Reticulated Single-Crystal Luminescent Screen," J. Electrochem. Soc., vol. 133, No. 7, pp. 1492-1497, Jul. 1986.

Jenmar Visual Systems, Sunnyvale, CA, 4 pages, no date, but at least as early as Oct. 15, 1998.

Landau, B.V. and Lissberger, P.H., "Theory of Induced-Transmission Filters in Terms of the Concept of Equivalent Layers," Journal of the Optical Society of America, vol. 62, No. 11, pp. 1258-1264, Nov. 1972.

Launer, Herbert F., "Exposure Meter for Precision Light Dosage", The Review of Scientific Instruments, vol. 20, No. 2, Feb. 1949, pp. 103-109.

Lissberger, P.H., "Coatings with Induced Transmission," Applied Optics, vol. 20, No. 1, pp. 95-103, Jan. 1, 1981.

Mauch, R.H., et al., "Optical Behaviour of Electroluminescent Devices," Springer Proceedings in Physics, vol. 38, Electroluminescence, © Springer-Verlag Berlin, Heidelberg, pp. 291-295 (1989).

Morgan, C. G., et al., "New Approaches to Lifetime-Resolved Luminescence Imaging", Journal of Fluorescence, vol. 7, No. 1, 1997, pp. 65-73.

Pelletier, E. and Macleod, H.A., "Interference Filters with Multiple Peaks," Journal of the Optical Society of America, vol. 72, No. 6, pp. 683-687, Jun. 1982.

Plasma Display Manufacturers of the American Display Consortium, "Recommended Research Topics on Plasma Display for the DARPA Sponsored Phosphor Center of Excellence," pp. 1-2, Mar. 24, 1993.

Poelman, D., et al., "Spectral Shifts in Thin Film Electroluminescent Devices: An Interference Effect," J. Phys. D: Appl. Phys., vol. 25, pp. 1010-1013 (1992).

Schott Glass Technologies, Inc., Schott Total Customer Care, Contrast Enhancement Filters, Duryea, PA, 6 pages, Jan. 1998.

Schubert, E.F., et al., "Giant Enhancement of Luminescence Intensity in Er-doped $Si/SiO_2$ Resonant Cavities," Appl. Phys. Lett. vol. 61, No. 12, pp. 1381-1383, Sep. 21, 1992.

Stewart Filmscreen Corporation®, www.stewartfilm.com, 34 pages website downloads as of Oct. 8, 1998.

Tuenge, R.T., "Current Status of Color TFEL Phosphors," Electroluminescence—Proceedings of the Sixth International Workshop on Electroluminescence, El Paso, Tex., pp. 173-177, May 1992.

Vlasenko, N.A., et al., "Interference of Luminescent Emission from an Evaporated Phosphor," Opt. Spect., vol. 11, pp. 216-219 (1961).

Vlasenko, N.A., et al., "Investigation of Interference Effects in Thin Electroluminescent ZnS-Mn Films," Opt. Spect., vol. 28, pp. 68-71 (1970).

Whitaker, Jerry C., "Electronic Displays: Technology, Design, and Applications," McGraw-Hill, Inc., pp. 185-192 (1994).

World Watch, Photonics Spectra, "IR Reflective Coating Boosts Bulb's Output, Recycling of IR Energy Saves Power, Cuts Costs" pp. 40-41, Jan. 1991.

Yamamoto, Y., et al., "Optical Processes in Microcavities," Physics Today, pp. 66-73, Jun. 1993.

Yokoyama, H., "Physics and Device Applications of Optical Microcavities," Science, vol. 256, pp. 66-70, Apr. 3, 1992.

Young, L., "Multilayer Interference Filters with Narrow Stop Bands," Applied Optics, vol. 6, No. 2, pp. 297-312, Feb. 1967.

European Patent Office, Extended European Search Report dated Jan. 5, 2016 for Application No. PCT/US2013/029931, 7 pages.

\* cited by examiner

FIG. 3
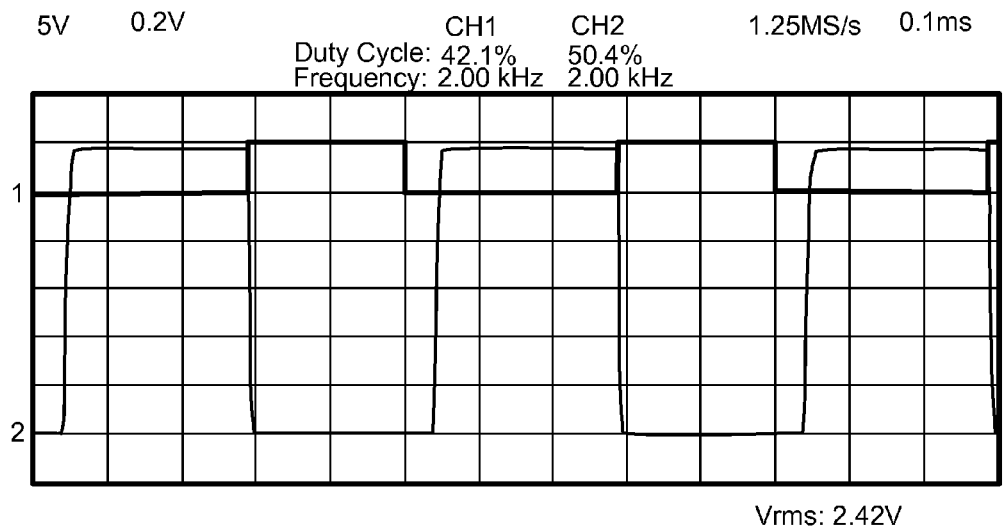
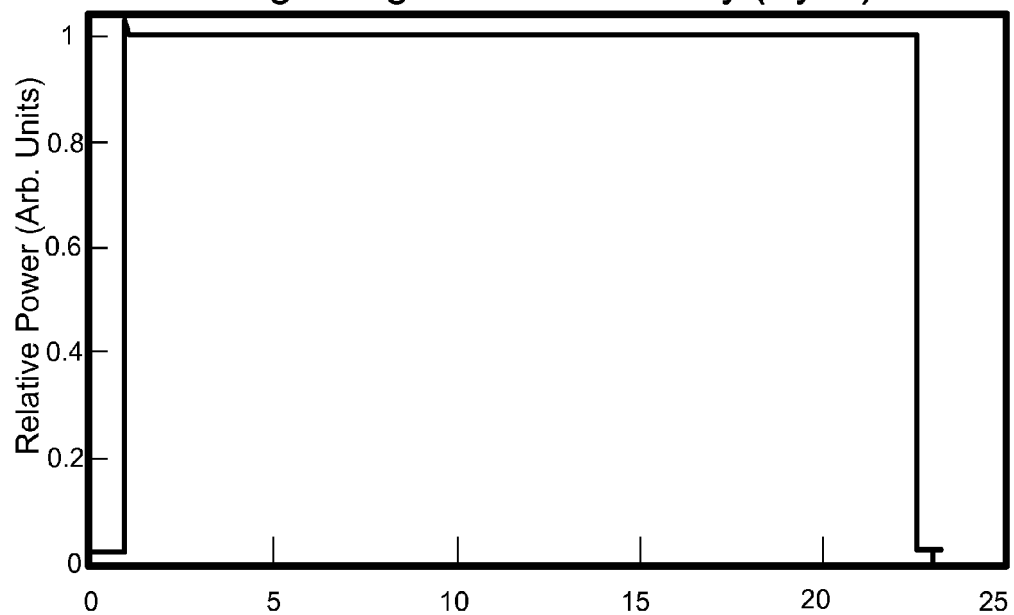
FIG. 4

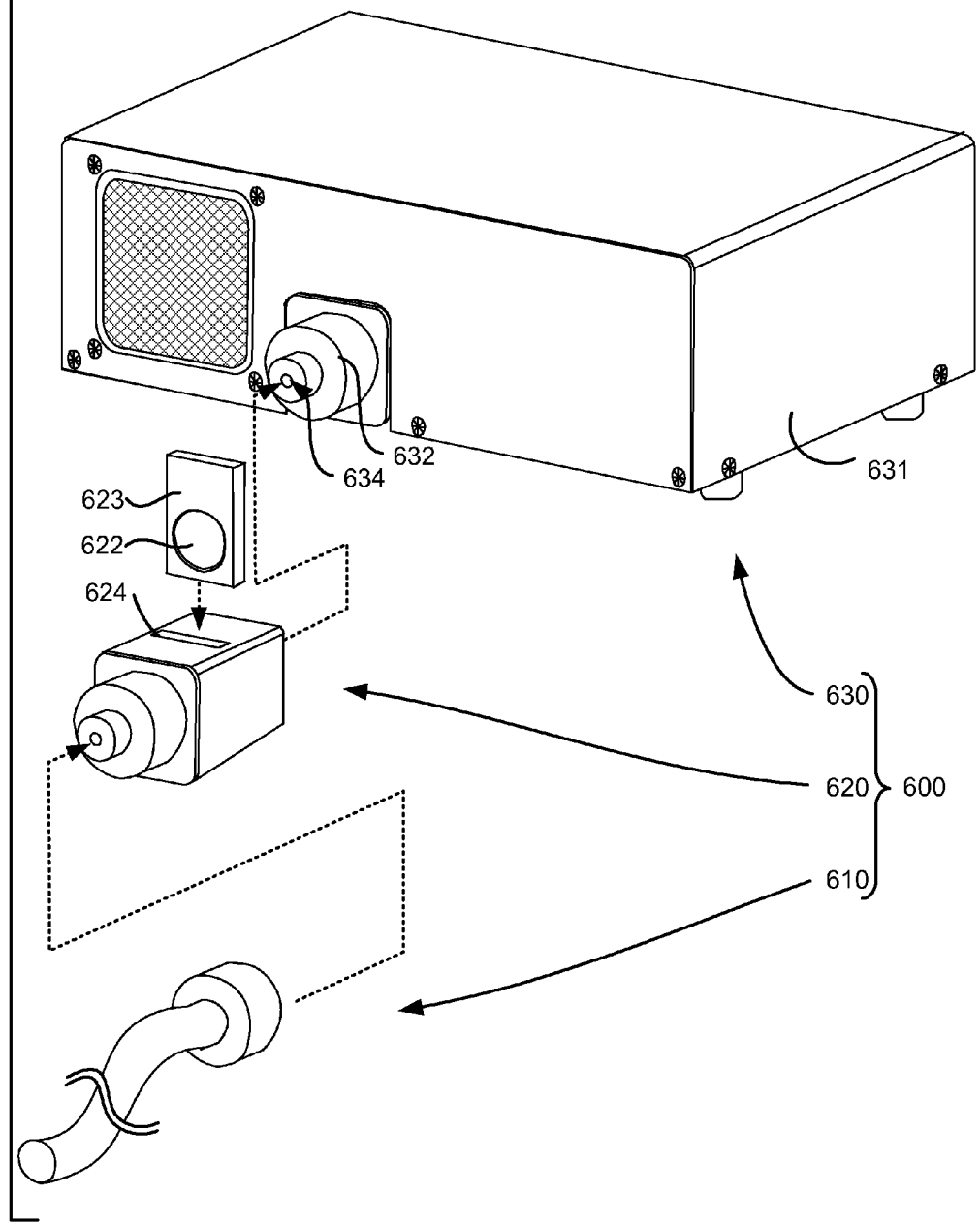

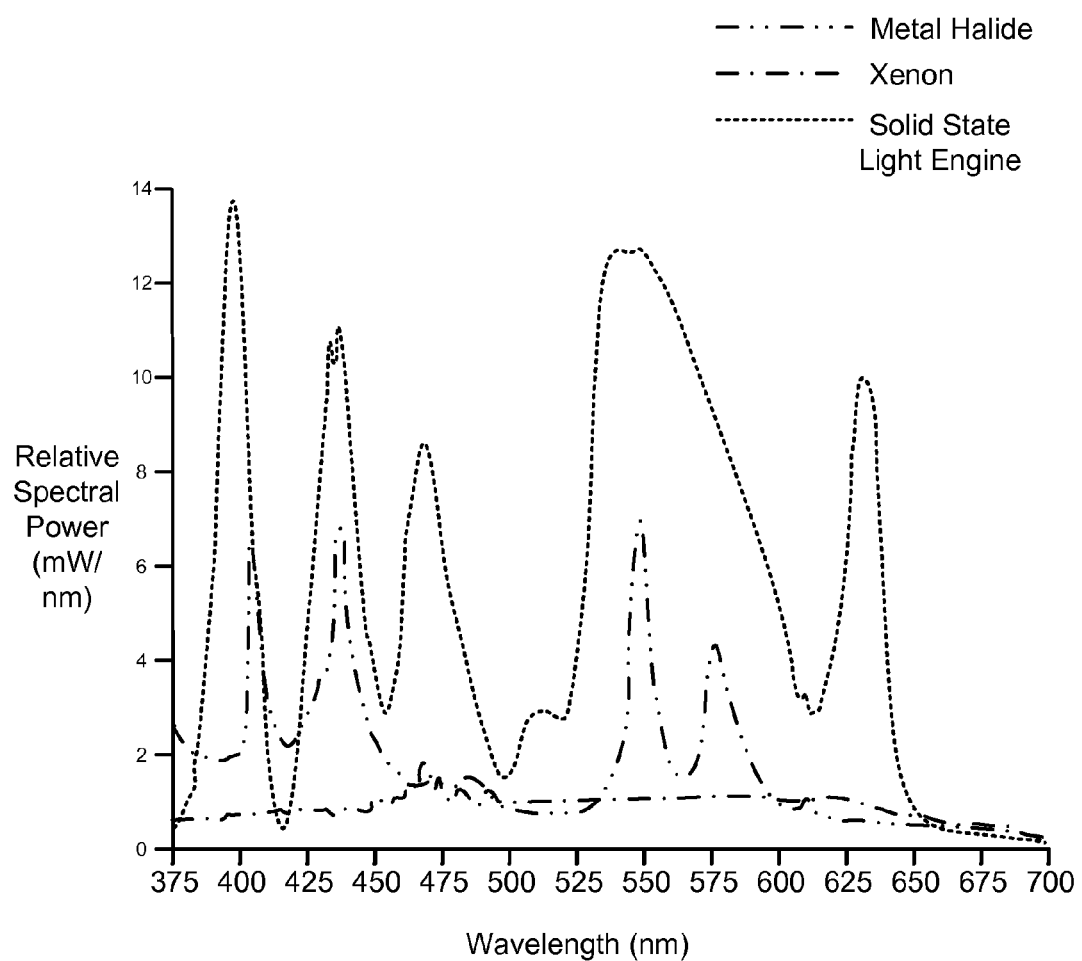

SOLID STATE CONTINUOUS WHITE LIGHT SOURCE

CLAIM OF PRIORITY

The present application claims priority to U.S. Provisional Patent Application No. 61/589,086, filed Jan. 20, 2012, entitled "SOLID STATE CONTINUOUS WHITE LIGHT SOURCE"; and U.S. Provisional Patent Application No. 61/644,921, entitled "SOLID STATE CONTINUOUS WHITE LIGHT SOURCE", filed May 9, 2012, which applications are incorporated herein by reference in their entireties.

RELATED APPLICATIONS

The present application is related to the following patent applications which are incorporated herein by reference:

U.S. Pat. No. 8,242,462, granted Jan. 1, 2010, entitled "Lighting Design of High Quality Biomedical Devices"; and U.S. Patent Application entitled "Bioanalytical Instrumentation Using A Light Source Subsystem," Publication No. 2007/0281322 filed May 21, 2007;

U.S. Patent Application entitled "Light Emitting Diode Illumination System," Publication No. 2009/0008573 filed Jul. 2, 2008;

U.S. Patent Application entitled "Light Emitting Diode Illumination System," Publication No. 2009/0040523 filed Aug. 5, 2008; and U.S. Patent Application entitled "Light Emitting Diode Illumination System," Publication No. 2011/0116261 filed Jan. 24, 2011.

FIELD OF THE INVENTION

The present invention relates to lighting systems for microscopy, fluorescence microscopy, and endoscopy. In particular the present invention relates to a solid state continuous white light source for microscopy and fluorescence microscopy.

BACKGROUND OF THE INVENTION

Among the trends redefining 21st century biomedical diagnostics and therapeutics is the design of low-cost portable analyzers. Because light is a powerful tool in many of today's most widely used life science instruments, high intensity, low cost light engines are essential to the design and proliferation of the newest bio-analytical instruments, medical devices and miniaturized analyzers. The development of new light technology represents a critical technical hurdle in the realization of point-of-care analysis.

Lighting for life sciences is a broad and general category. Not only are the source specifications varied but so too are the equally important optical delivery requirements. Spectral and spatial lighting requirements for sensing on the head of an optical probe or within a single cell in a flowing stream differ in output power by orders of magnitude from the requirements of a multi-analyte detection scheme on an analysis chip or within the wells of a micro-titer plate. The number of colors, spectral purity, spectral and power stability, durability and switching requirements are each unique. Illuminating hundreds of thousands of spots for quantitative fluorescence within a micro-array may be best served by projection optics while microscopes set demanding specifications for light delivery to overfill the back aperture of the microscope objective within optical trains specific to each scope body and objective design.

Historically arc lamps are noted to be flexible sources in that they provide white light. The output is managed, with numerous optical elements, to select for the wavelengths of interest and for typical fluorescence based instruments, to discriminate against the emission bands. However their notorious instability and lack of durability in addition to their significant heat management requirements make them less than ideal for portable analyzers. Moreover, large power demands to drive them present a barrier to battery operation within a compact design.

Lasers require a trained user and significant safety precautions. While solid state red outputs are cost effective, the shorter wavelength outputs are typically costly, require significant maintenance and ancillary components. Color balance and drift for multi-line outputs is a serious complication to quantitative analyses based on lasers. Moreover, the bulk of fluorescence applications do not need coherent light, are complicated by speckle patterns and do not require such narrow band outputs. Overcoming each of these traits requires light management and adds cost to the implementation of lasers for most bio-analytical tools.

Finally LEDs have matured significantly within the last decades. LEDs are now available in a relatively wide range of wavelengths. However their output is significantly broad so as to require filtering. Additionally, output in the visible spectrum is profoundly reduced in the green, 500-600 nm. The LED also presents trade-offs with respect to emission wavelength dependent intensity, broad emission spectrum (spectral half width on the order of 30 nm or more), poor spectral stability, and the wide angular range of emission. In addition, the process used to manufacture LED's cannot tightly control their spectral stability; anyone wishing to use LED's in applications requiring a good spectral stability must work directly with a supplier to essentially hand-pick the LED's for the particular application. Finally, LED's generate light over a wide angular range (50% of light intensity emitted at) 70°. While optics can narrow the emission band and focus the light output, the resulting loss in power and increase in thermal output further limit the feasibility of LED light engines.

Most importantly, these light technologies cannot be readily improved for bioanalytical applications. The associated light engine market simply does not justify the large investment necessary to overcome fundamental performance limitations. As a result, analytical instrument performance and price is constrained by the light source with no clear solution in sight. Moreover the numerous manufacturers of lamps and lasers provide only a source, not an integrated light engine. Companies such as ILC Technology, Lumileds, Spectra-Physics, Sylvania and CooILED require some sort of mechanics and or electro-optics such as acousto-optic tunable filters (AOTFs), excitation filters (with a wheel or cube holder), shutters and controllers.

SUMMARY OF THE INVENTION

The present invention provides an inexpensive lighting solution, uniquely well suited to the production of safe, effective and commercially viable life science tools and biomedical devices attained using the solid-state white light engine as described. In an embodiment of the invention, this light engine can provide powerful, pure, stable, inexpensive light across the visible spectrum. Light engines are designed to directly replace the entire configuration of light management components with a single, simple unit. Power, spectral breadth and purity, stability and reliability data will demonstrate the advantages of these light engines for today's bioanalytical needs. Performance and cost analyses can be compared to traditional optical subsystems based on lamps, lasers and LEDs with respect to their suitability as sources for biomedical applications, implementation for development/evaluation of novel measurement tools and overall superior reliability. Using such sources the demand for portable, hand-held analyzers and disposable devices with highly integrated light sources can be fulfilled.

Embodiments of the present invention are directed to a solid state white-light subsystem suitable for use as a replacement for conventional arc light, Metal Halide and Xenon white-light subsystems for applications in microscopy, fluorescence microscopy, and endoscopy. In particular embodiments, the solid state light subsystem generates white light which is continuous in the visible spectrum from 380 nm to 650 nm. In particular embodiments the solid state white-light subsystem incorporates one or more light pipe engines.

In particular embodiments the present invention is directed to a to a solid state white-light subsystem which emits whit light having a spectral power equal to or greater than the spectral power of a 120 W metal halide lamp or 150 W Xenon lamp across substantially the entire visible spectrum from 380 nm to 650 nm. In particular embodiments the spectral power is greater than 1 mW/nm over the substantially the entire visible spectrum from 380 nm to 650 nm and greater than 3 mW/nm over the range from 500-600 nm.

In an embodiment of the present invention, an illumination system can emit high quality white light. In an embodiment of the present invention, the illumination system can be pulsed on and off as desired to reduce heat generation. In an embodiment of the present invention, an illumination and collection system can be pulsed on and off to allow time-based fluorescence detection.

Other objects and advantages of the present invention will become apparent to those skilled in the art from the following description of the various embodiments, when read in light of the accompanying drawings.

BRIEF DESCRIPTION OF THE FIGURES

Various embodiments of the present invention can be described in detail based on the following figures, wherein:

FIG. 3 shows light pipe engine with <10 ns rise and fall times for fast switching between bands;

FIG. 4 shows light engine stability over 24 hours of use;

FIG. 6A shows a white light illumination system according to an embodiment of the present invention;

FIG. 6C is a graph showing spectral power of the solid state white light subsystem of FIG. 6B in comparison to a 120 W metal halide lamp and a 175 W Xenon lamp.

DETAILED DESCRIPTION OF THE INVENTION

Figure 1:
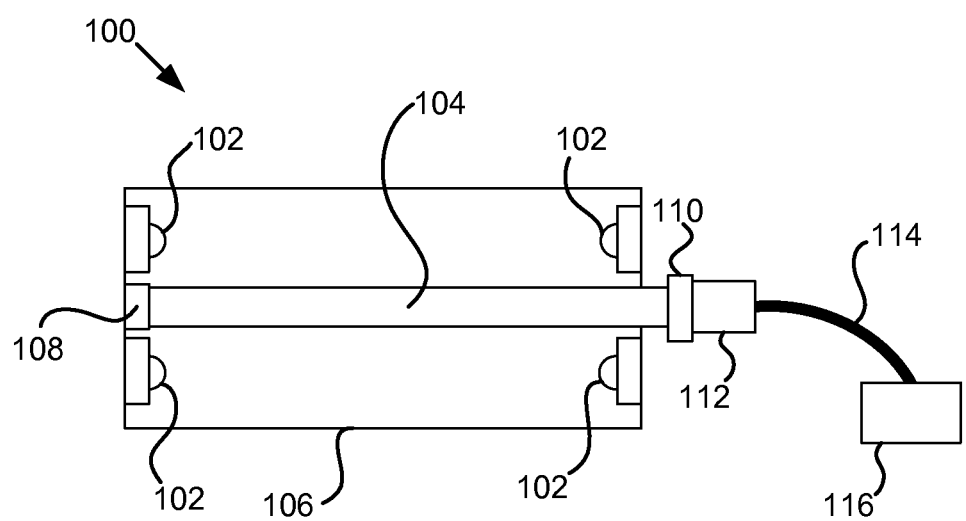
FIG. 1 shows a schematic of a light engine subsystem consisting of a lamp module and delivery optics.

While lighting manufacturers cannot provide all things to all applications, it is precisely this breadth of demand for which a light engine can be designed. To that end, products are not simple sources, but rather light engines: sources and all the ancillary components required to provide pure, powerful, light to the sample or as close to it as mechanically possible. Such designs have resulted in products that embody a flexible, hybrid solution to meet the needs of the broad array of applications for biotech. A qualitative comparison of light engine performance as a function of source technology is summarized in Table 1.

TABLE I

A qualitative comparison of light engine performance as function of the source technology employed

| Source Technology | Useable Light | Uniformity | Temporal Response | Heat Generation | Durability | Cost |
| --- | --- | --- | --- | --- | --- | --- |
| Arc Lamp | med | poor | none | high | low | high |
| Laser | high | poor | none | low | low | very high |
| LED | low | poor | fast | low | high | medium |
| Tungsten | low | poor | none | medium | low | medium |
| Light Pipe | high | high | fast | low | high | low |

Light Pipe Engines

While no one lighting solution can best satisfy all instrument architectures, a light pipe engine combines the best of solid state technologies to meet or outperform the traditional technologies listed in Table I on the basis of all figures of merit for all individual wavelengths. Key to this performance is the light pipe architecture. Single outputs, such as red from a diode laser, may be competitive. However, no family of outputs can by assembled that bests the light pipe disclosed herein. In an embodiment of the invention, a light pipe engine can emit narrowband light exceeding 500 mW/color with intensifies up to 10 W/cm$^2$ depending on the application. In an embodiment of the invention, bandwidths as narrow as 10 nm are achievable. While such output power and overall emission intensity is impressive, the most significant figure of merit for quantifying the value of any lighting subsystem for bio-analytics is the intensity of high quality illumination provided to the sample. This is a factor dictated by the instrument design and sample volume and clearly very application specific.

In the case of medical devices and portable diagnostics the present light pipe invention offers a smart alternative for light generation. The light pipe engine is an optical subsystem; it consists of lamp modules for each discrete output based on solid state technologies tailored to best satisfy that output requirement complete with collection and delivery optics. The capabilities of the light pipe engine are highlighted in Table 2. The high performance illumination provided by the light pipe engine is embodied in a single compact unit designed to replace the entire ensemble of lighting components. The sources, excitation filters, multicolor switching capabilities and fast pulsing are contained within one box such that no external optics or mechanics are required.

TABLE II

Light pipe engine metrics of light pipe engines designed to meet the needs for portable fluorescence assays and biomedical devices.

| Key Metrics: | |
|---|---|
| Spectral Output | Up to eight colors spanning UV-Vis-NIR<br>>_ 100 mW/spectral band<br>1-10 W/cm |
| Peak Wavelength | Optimal for different floors, adjustable bandwidths |
| Power Stability | >99% over 24 hours |
| Spectral Width | 10 to 50 nm |
| Spectral Drift | <1% in 24 hours |
| Color Dependence | None |
| Lifetime | >5000 hrs |
| Footprint | amenable to portability |
| Maintenance | None, no replacement components for the light engines lifetime |

In various embodiments of the present invention, a lamp emits wavelengths of light, which excite fluorescence from photosensitive targets in the sample of interest. In various embodiments of the present invention, a lamp can be in the form of a tube, rod, or fiber of varying or constant diameter. In various embodiments of the present invention, a constituent light pipe can be made of glass, plastic, single or multiple inorganic crystal(s), or a confined liquid. In various embodiments of the present invention, a pipe either contains or is coated with a layer or layers containing, a narrow band luminescent material such as organic or inorganic compounds involving rare earths, transition metals or donor-acceptor pairs. In various embodiments of the present invention, a lamp emits confined luminescence when excited by IR, UV, or visible light from an LED, Laser, fluorescent tube, arc lamp, incandescent lamp or other light source. In an embodiment of the present invention, a lamp operates through the process of spontaneous emission, which results in a much larger selection of available wavelengths than is available for efficient stimulated emission (laser action). A number of lamps each emitting one or more color of light can have their constituent light pipes coupled in parallel or in series acting to produce multiple colors simultaneously or in sequence. Lamps can be illuminated continuously or can be pulsed on and off rapidly to enable time-based detection methods. A lamp can be switched off between measurements, to eliminate the heat output. This can be contrasted with alternatives such as arc lamps or lasers that are unstable unless they are operated continuously.

Shown in FIG. 1, is the light pipe engine 100 of an embodiment of the invention. An individual lamp module driven by light pipe technology consists of an excitation source 102, typically one or more LEDs, and a light pipe 104. In an embodiment, the excitation source 102 and light pipe 104 can be housed in a cylindrical waveguide 106. The excitation source 102 drives luminescence in the light pipe 104, which is composed of a glass or polymer fiber. In an embodiment, light pipe 104 includes a mirror 108. Glass fibers are either doped with a rare earth metal or activated with a transition metal. Polymer fibers are doped with a dye. The fibers have fast response and decay times and can achieve a high efficiency through the design of delivery optics. The design and selection of the fiber determines the peak wavelength of the output illumination; options exist to span the UV-Vis-NIR spectrum. The bandwidth of the luminescence is narrow and can be further defined with the use of band pass filters 110 integrated into the delivery optics. In an embodiment, the delivery optics may include a band pass filter 110 connected to a coupler 112, which can be attached to an optical delivery pipe 114 which leads to an instrument (e.g., a microtiter plate) 116. Output intensity is determined through the design of the pipe's excitation source.

The light pipe geometry provides a unique opportunity to shape and direct the angular and spatial range of outputs. Combined with a high output power, the delivery optics can be readily tailored to couple the light with various instruments and analyzers. Sensors, optical probes, microscope objectives or through liquid light guides, two-dimensional oligomer and micro fluidic chips, and micro titer plates are all illumination fields that light pipe engines can readily support. Moreover, high output power enables illumination of large areas within a chip, micro array or micro titer plate and, as a result, support high-speed throughput in instruments where to date only scanning modes of operation could be envisioned.

The preferred mode of light pipe excitation is the application of one or more LED's. This approach takes advantages of the benefits of LED illumination: low cost, durability, and, at an appropriate excitation wavelength, high output power to drive the light pipe. In so doing the LED's shortcomings are managed. The lack of spectral stability and the high angular output characteristic of LED's do not impact the luminescence of the light pipe. Instead, the innovation of the light pipe enables circumvention of the principle of etendue conservation. All light sources must conform to this dictate, which requires the spread of light from a source never exceed the product of the area and the solid angle. Etendue cannot decrease in any given optical system.

The ability to modulate solid-state source outputs provides a unique opportunity for multiplexed fluorescent assays. Current light engine designs employ solid state materials with fast luminescence (approximately 10 ns.) The light pipe and LED have similar modulation capabilities thus multiple light pipes tuned to different output wavelengths can be employed to selectively detect multiple fluorescent tags within a given analysis. In addition, pulse modulation and phase modulation techniques enable fluorescence lifetime detection and afford improved signal to noise ratios. Each of the solid state units is truly off when it is off so low background signals and high contrast ratios are possible.

Table III shows an embodiment of the present light pipe engine invention's product and performance features. As improvements are made to LED's and the cost of semiconductor lasers continue to decline, the tool chest of options available to light pipe engines will continue to evolve. The desired light engine can ultimately be powered by a combination of light pipe, LED's and lasers. The knowledge and competency to integrate any of these lighting technologies into the delivery optics supports the requirements of each specific application and provides technical and commercial value.

TABLE III

The light pipe engine feature set.

| Wavelengths | UV - Vis - NIR |
|---|---|
| Colors | Up to eight |
| Intensity | 1-10 W/cm$^2$ |
| Bandwidths | Adjustable |

TABLE III-continued

The light pipe engine feature set.

| | |
|---|---|
| Size | Compact |
| Ease of Use | Yes |
| Modulation | Up to 5 kHz |
| Color control | Independent |
| System Control | Manual or computer |
| Heat output | Minimal |
| Life time | Long |

Spectral Bands and Output Power

Figure 2:
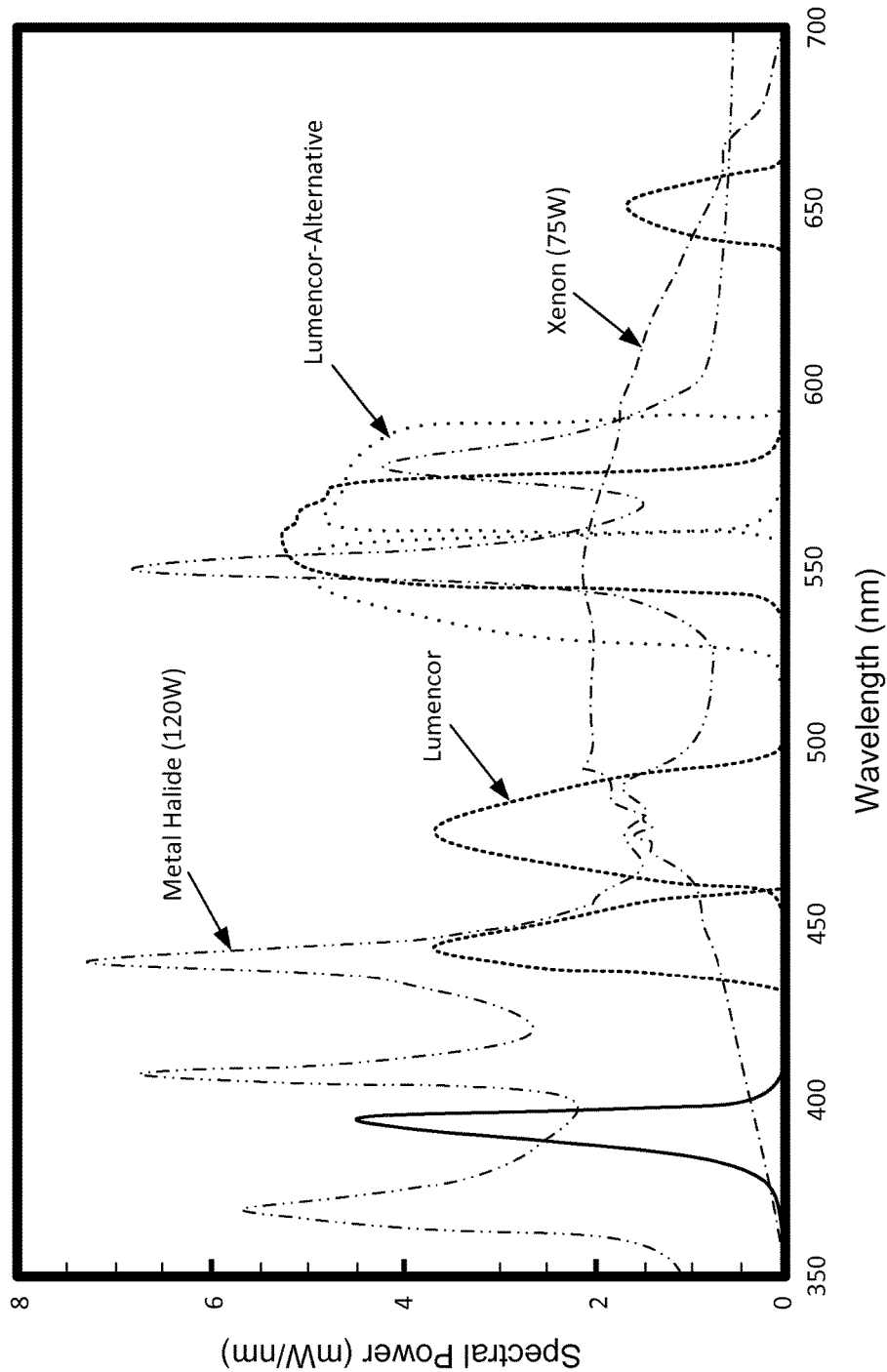
FIG. 2 shows light engine output relative to a typical metal halide lamp and 75 W xenon bulb.

In various embodiments of the present invention, the light pipe engine performs well compared with the output power across the visible spectrum to other lamps (see "Lumencor" in FIG. 2). Such comparisons beg for disclaimers as the outputs of the commonly employed lamps change in time and degrade with usage. The light pipe engine is all solid state so they it is significantly more stable and reproducible. FIG. 2 was taken within the manufacturers' specified lifetime for each lamp, by an independent user well trained in biophotonics, these outputs represent typical performances of a common metal halide bulb, 75 W xenon bulb and that of the light pipe engine.

Such output comparisons are further complicated by mismatches between the spikes of the metal halide bulb and light pipe light engine output bands. However, noting such disparities it is fair to claim the outputs of the light engine across the visible spectrum compare well against the outputs of a metal halide bulb in spectral windows that match the excitation energies of some of the most commonly used fluors for biotech: around 390 nm where DAPI and Hoescht can be excited; in the window most commonly associated with a cyan line of an argon ion laser and often used to excite Alexa dyes, green fluorescent proteins and fluoresceins; and in the red where neither of the lamps provides appreciable power for the likes of Cy5. The light engine also bests the Xenon lamp across the palate of excitation wavelengths most common to biotech: the Xenon lamp underperforms particularly in the violet, cyan, blue and red regions of the visible spectrum. Of course, more powerful Xenon lamps are often employed to provide enhanced performance at a significant maintenance cost.

In another embodiment of the present invention, as seen in FIG. 2 (see line "Lumencor-Alternative"), the output of the green and amber bands have essentially doubled, such that on a photon per photon basis the area under the curve for the arc lamp vs. light engine are the same. Certainly the peak shapes, and figures of merit (height, FWHM, etc.) differ. However, no compromise in output power, even for the 546 nm band of the arc lamp, should be incurred as a consequence of using a light pipe engine replacement.

Alternatively, a light pipe engine can be employed in a short duty cycle mode for power starved applications. When feasible, pulse widths of less than 100 ms at 10% duty cycles can actually improve the power output per band by a factor of 1.5 to 2.0 over longer duty cycles or in continuous mode of operation. Applications that employ multiple lasers and acousto-optic tunable filters (AOTFs) but need safe, cost effective and easy to employ lighting solutions might benefit from such light engine performance. Fluorescence microscopy for multicolor detection could take advantage of this option, for example. As could numerous other bioanalytical platforms such as a light engine replacement for the optical excitation from AOTF-based multicolor fluorescence detection for short tandem repeat (STR) analysis in a microeletrophoretic device, a glass microchip.

Fast Switching

Because of the solid state nature and independently operable designs of the lamp modules, coupled to fast (approximately 10 ns) decay times of typical materials employed, a light pipe based light engine outperforms any broad spectrum source in terms of support for fast analyses. Lamp based sources are coupled to filters and/or shutters with mechanical supports that relegate them 1 to 50 millisecond regimes. Even LED based lamps require filtering for most quantitative fluorescence based analyses. The light pipe based light engine incorporates all that filtering into its highly integrated design. Therefore switching times are limited today by the electronics of the boards controlling the sources. Rise times of less than 20 µs and fall times of less than 2 us are typical (see FIG. 3). Moreover each color can be switched independently and is compatible with triggering by TTL, RS232 and USB and intensity control by RS232, USB or manually. This supports experiments where simultaneous excitation of multiple tags could previously only be done with multipass excitation filters and broadband sources. Using a light pipe engine, effectively instantaneous excitation of individual reporters can be manipulated within microsecond time frames to achieve rapid, serial exposure of a biologic event to the various excitation bands with no external hardware beyond the light engine itself.

Stability

Because a light pipe based light engine is based on solid state technologies, they are extremely stable both in short duration experiments and over long term use. FIG. 4 depicts this stability. Light engines are powered by 24 V power supplies operated in DC mode, therefore there is no 60 Hz noise. All colors perform similarly. In 24 hours of continuous operation, the output fluctuates on the order of 1%. Short term stability on the order of 1.0 ms is approximately 0.5%. Short term stability for 0.1 ms is diminished by a factor of ten to 0.05%.

Eight Color Light Engine Subsystem

Figure 5:
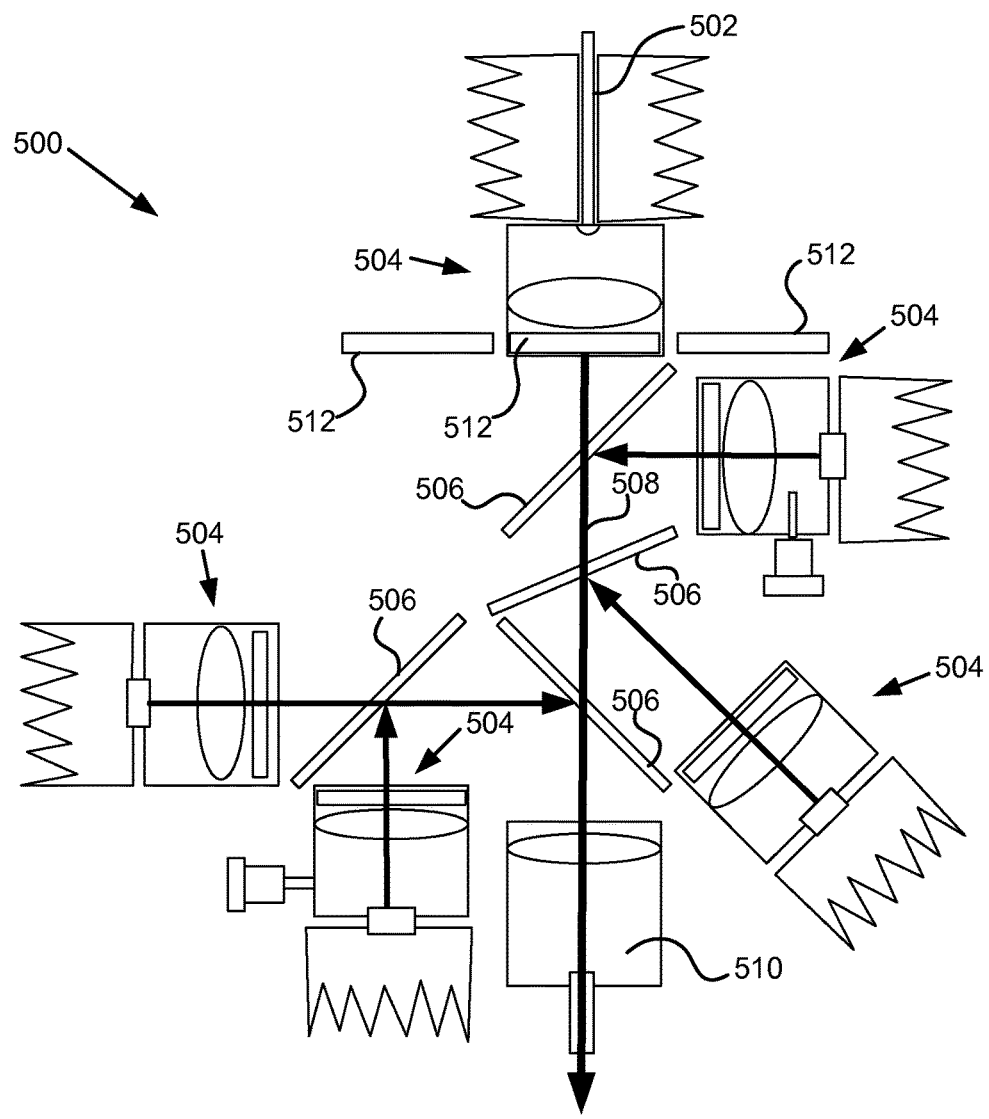
FIG. 5 shows a eight color light engine layout, including a light pipe and five other solid state light sources, with dichroic mirrors to create a single coaxial 8-color beam.

FIG. 5 shows a schematic for a eight color light engine layout. In an embodiment of the invention, a eight color light engine 500 includes a luminescent rod 502 and five other solid state light sources 504, with dichroic mirrors 506 to create a single coaxial 8-color beam 508 (for example selected from UV 395, Blue 440, Cyan 485, Teal 515, Green 550 or 575, Orange 630 and Red 650 nm) leading to an output 510. Each individual light source is collimated so as to be efficiently combined and after color combination, the beam is refocused into a light guide for transport to the device or system to be illuminated according to an embodiment of the invention. In this embodiment, a manual or electromechanical filter slider 512 allows green yellow filtering of YAG generating 550 or 575 nm light. Additional colors can be used. For example, a color band centered at 550 nm can be replaced with a color band centered at 560 nm. Each individual light source is collimated so as to be efficiently combined and after color combination, the beam is refocused into a light guide for transport to the device or system to be illuminated according to an embodiment of the invention.

The light engine subsystem is designed to interface to the array of bioanalytical tools with the expectation that the end user can take for granted the high quality of the illumination. Table IV summarizes four bioanalytical applications for which light engines including light pipes could replace more traditional illumination subsystems and offer performance and cost advantages. For example, Kohler illumination in transmitted light microscopy requires that the light be focused and collimated down the entire optical path of the microscope to provide optimal specimen illumination. Even light intensity across a fairly large plane is a critical requirement. For stereomicroscopy, lighting is achieved with ringlights at the objective and fiber optic lights pointed at the specimen from the side. In both cases, the light engine must efficiently couple to a fiber optic cable.

In a preferred embodiment the total output power is approximately 2.5 W. Advantageously, the spectral power of the solid state illumination system 600 is equal to or greater than the spectral power of a 120 W metal halide lamp or 150 W Xenon lamp across substantially the entire visible spectrum from 380 nm to 650 nm. This solid state light source

TABLE IV

Performance and cost analysis of the light pipe engine vs. traditional illumination subsystems in four key bioanalytical applications

| specification | Sanger Sequencing | | Q-PCR | | Flow Cytometry | | Fluorescence Microscopy | |
|---|---|---|---|---|---|---|---|---|
| Light engine | Light Pipe | Ar Ion Laser | Light Pipe | Metal Halide | Light Pipe | Lasers | Light Pipe | Metal Halide |
| Intensity W/cm$^2$ | 150-250 | 150-250 | 0.5-1 | 0.2-1, very λ specific | 150-250 | 150-250 | <50 | 1-50, very λ specific |
| Wavelength | 505 nm | multiline | 4 colors | | >2 colors | | 4 colors | |
| Bandwidth, nm | 10-30 | 26 | 10-30 | 15 | 10-30 | <5 | 10-30 | 15 |
| Stability | 0.1% | >1% | 0.1% | >1% | 0.1% | >1% | 0.1% | >1% |
| Switching, ms | <0.03 | 1-10, ext. shutter | <0.03 | 40, ext. shutter | <0.03 | 1-10, ext. shutter | <0.03 | 40, ext. shutter |
| MTBF, hrs | >10,000 | <4,000 | >10,000 | <1,000 | >10,000 | <4,000 | >10,000 | <1,500 |
| Price | <$3K | >$5K | <$7.5K | >$10K | <$5K | >$5K | <$7.5K | >$10K |

For portable diagnostic tools, the delivery optics must provide even illumination over a small volume. These requirements are similar to, but less restrictive than those presented by capillary electrophoresis. Capillary electrophoresis requires an intense (10 mW) light focused onto the side of a capillary tube with characteristic dimensions on the order of a 350 pm outer diameter and a 50 pro inner diameter. To achieve this goal, the delivery optics were comprised of a ball lens to collect and collimate light from the lamp module (already coupled into an optical fiber), a bandpass filter to provide a narrow bandwidth of illumination, and an aspheric lens to focus the light at the center of the capillary bore. This approach yielded an 80 pin spot size and the desired 10 mW of delivered power to the capillary tube.

The design of delivery optics for microfluidic immunoassays requires both the even illumination required for optical microscopy and the small volume illumination required for capillary electrophoresis. Light engines capable of delivering even illumination at the active sites in a microfluidic array for detection of fluorescent tagged biomarkers have been designed for immunochemical as well as genomic applications. The advantages of the luminescent light pipe are providing commercial, readily available light engine solutions for illumination-detection platforms optimized for portable diagnostic tools.

Solid State Source of Continuous White Light

Figure 6B:
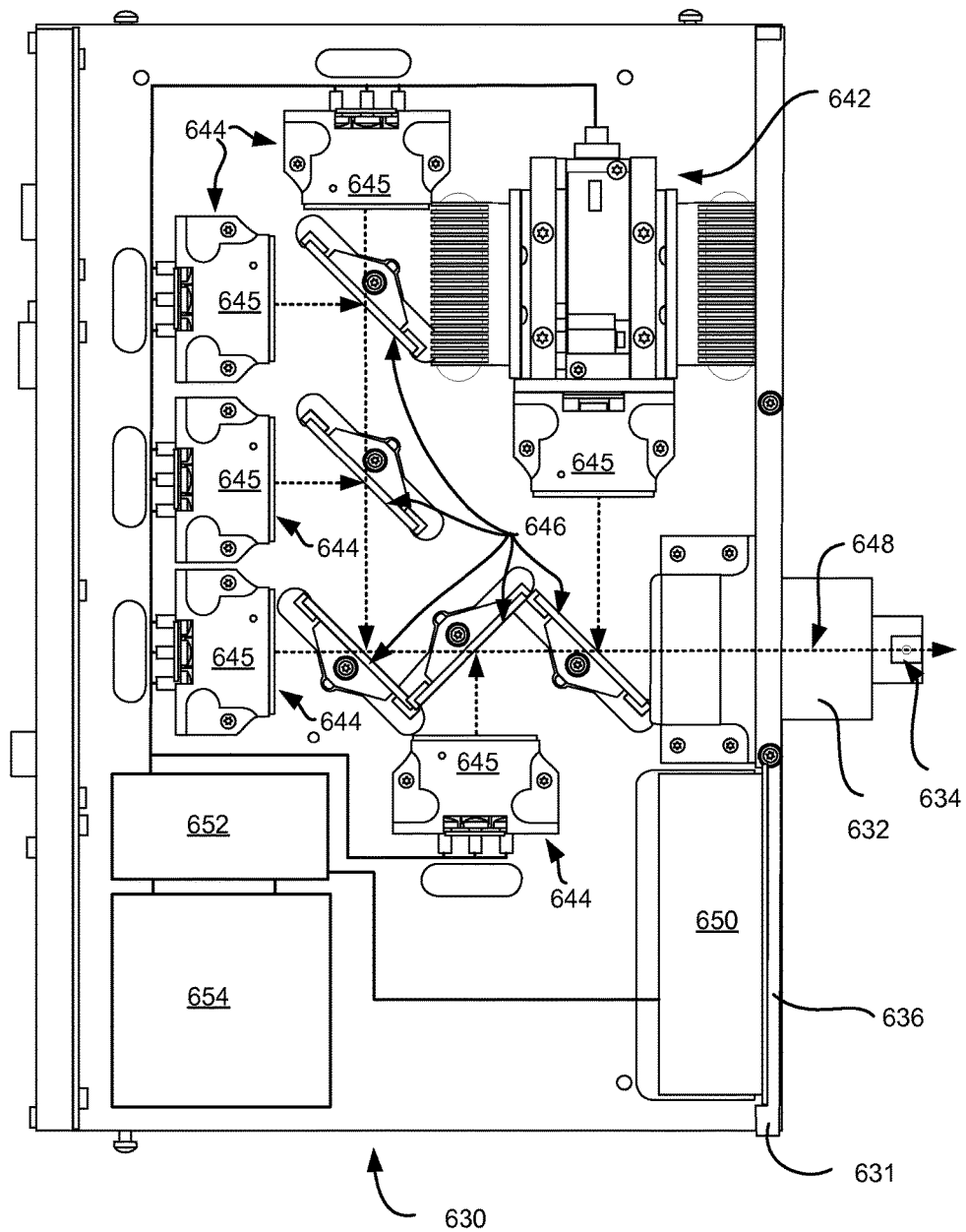
FIG. 6B shows a plan view of the components of the solid state white light subsystem of the white light illumination system of FIG. 6A.

FIGS. 6A-6C shows aspects of a solid state illumination system 600 suitable for use as a replacement for conventional arc light, Metal Halide and Xenon white-light sources for applications in microscopy, fluorescence microscopy. The solid state illumination system utilizes multiple solid state light sources operating simultaneously to generate one white light output. The solid state illumination system 600 generates white light which is continuous in the visible spectrum from 380 nm to 650 nm, has a high color rendering index, including ultraviolet, and is suitable for imaging all the most common fluorophores and fluorescent proteins. The white light can be modulated using external bandpass filters.

of the present invention is substantially different that prior art devices for microscopy that provide light of a selected color for microscopy rather than providing continuous spectrum white light which can be externally filtered downstream—for example using filter systems previous only suitable for arc lamps—thus the user can utilize a broad range of commercially available filters. This provides the most flexibility to the user in utilizing the light output.

FIG. 6A shows the solid illumination system 600; FIG. 6B shows a plan view of the components of the solid state light engine 630 of the solid state illumination system of FIG. 6A; and FIG. 6C is a graph showing spectral power of the solid state light engine of FIG. 6B in comparison to a 120 W metal halide lamp and a 175 W Xenon lamp. Referring first to FIG. 6A which shows solid state illumination system 600. As shown in FIG. 6A, solid state illumination system 600 includes a flexible fiber optic 610, a filter system 620, and a solid state light engine 630. Solid state light engine 630, includes a liquid light guide 632 mounted on the exterior of housing 631 of solid state light engine 630. Liquid light guide 632 includes an aperture 634 through which white light is provided from solid state light engine 630. Liquid light guide 632 includes a coupling for connecting external filter system 620 and/or flexible fiber optic 610 to solid state light engine 630 such that white light from aperture 634 is efficiently coupled to external filter system 620 and/or flexible fiber optic 610. A grill 636 allows flow of air through housing 631 for cooling the light sources.

Filter system 620 includes one or more light filters 622 which can be placed in the path of the white light exiting from aperture 634. As shown in FIG. 6A, filter system 620 includes a slot 624 designed to receives a filter paddle 623 holding a light filter 622. A range of filter paddle/filter combinations is provided in order that a user can modify the white light according to the users needs. Alternatively, an automated and/or computer controlled filter system can be utilized. For example a motorized filter wheel including a plurality of different filters can be used—a controller allows the selection and positioning of the desired filter in the light path. Alternatively, in some embodiments filter system 620 can comprise a filter cube including a dichroic mirror mounted on an optical block for use in fluorescence microscopy. Such filter cubes are typically mounted directly to the microscope rather than the solid state light engine 630. Advantageously, by providing continuous white light as an output the solid state light engine 630 allows for the use of conventional filter systems utilized with arc lamps.

Flexible fiber optic 610 is used to connect solid state light engine 630 to an optical system such as a microscope or endoscope. Adapters are provided to connect flexible fiber optic 610 to a range of microscope, endoscope and/or other desired optical systems requiring illumination. Flexible fiber optic 610 transmits light from solid state light engine 630 along its length to the optical system through optical fibers and or a liquid medium. Flexible fiber optic 610 is in some case connected between solid state light engine 630 and filter system 620 (for example where filter system 620 is mounted directly to a microscope. In other cases, flexible fiber optic 610 is connected to a coupling of filter system 620 as shown in FIG. 6A.

The light engine subsystem is designed to interface to the array of bioanalytical tools with the expectation that the end user can take for granted the high quality of the illumination. Table IV (above) summarizes four bioanalytical applications for which light engines including light pipes could replace more traditional illumination subsystems and offer performance and cost advantages. For example, Kohler illumination in transmitted light microscopy requires that the light be focused and collimated down the entire optical path of the microscope to provide optimal specimen illumination. Even light intensity across a fairly large plane is a critical requirement. For stereomicroscopy, lighting is achieved with ringlights at the objective and fiber optic lights pointed at the specimen from the side. In both cases, the light engine must efficiently couple to a fiber optic cable and thence to the particular bioanalytical tool.

FIG. 6B shows a plan view of the components of the solid state light engine 630 of the solid state illumination system. As shown in FIG. 6B, housing 631 contains a light pipe engine 642, and five LED light sources 644, and a plurality of dichroic mirrors 646. Each individual light source is collimated so as to be efficiently combined and after color combination, the beam is refocused into a light guide for transport to the device or system to be illuminated. The light pipe engine 642 and the LED light sources 644 each include output optics 645 to image and collimate the light output of the source into a beam that can be imaged on the input aperture of the liquid light guide 632. The light pipe engine 642, the LED light sources 644, and dichroic mirrors 646 are arranged to create a single coaxial beam of light 648 which is directed at the input aperture of the liquid light guide 632 as shown by the dashed arrows. In a preferred embodiment, the light beam 648 output is white light which is substantially continuous over the visible spectrum of 380 nm-680 nm and includes no ultraviolet or infrared light.

Housing 631 also contains a fan 650, controller 652, and power supply 654. Housing 631 can also contain one or more sensors (not shown) to analyze the spectral content of beam 648. Power supply can be an AC/DC transformer for wired applications or may alternatively be a battery for portable applications.

LED light sources 644 and light pipe engine 642 are selected to provide different color components of the spectral content of the continuous white light output. In a preferred embodiment there are five LED light sources 644 each producing a different color component of the continuous white light output. The output wavelengths of the sources overlap and combine to some extent contributing the overall spectral output of the solid state light engine 630. The LED light sources are ganged together and with the light pipe engine 642. In embodiments the LED light sources 644 and light pipe engine 642 produce spectral components centered on colors violet 395 nm, blue 425-460 nm, cyan 460-500 nm, teal 515 nm, green 500-615 nm, and red/orange 615-685 nm. All of LED light sources 644 and light pipe engine 642 are turned on at the same time such that the different colors are combined to create a substantially continuous white light having a high color rendering index (CRI). In alternative embodiments, a second light pipe engine 642 can be used in place of one or more of the direct LED light sources 644.

In a preferred embodiment light pipe engine 642 is used to generate green (green and yellow) light spanning 500-600 nm. LED lights that emit green light at high power are notoriously difficult to create—the so-called green gap. Thus light pipe engine 642 utilizes high power blue LED light sources to excite a luminescent rod which emits green light spanning 500-600 nm. In a preferred embodiment light pipe engine utilizes two arrays of 40 blue LEDs to excite emission of green light from the luminescent rod. A suitable light pipe engine 100 is described above with respect to FIG. 1. Suitable light engines are also described in the Related Applications listed above and incorporated herein by reference. The luminescent rod of the light pipe engine can be convectively cooled as previously described or conductively cooled by being clamped into contact with a metal pedestal heat sink (for example a copper heat sink.) A light pipe engine operating to generate green light allows the solid state light engine 630 to produce an output in the green and amber bands that is the same or greater than commonly used arc lamps (see, e.g. FIG. 6C). Thus, no compromise in output power, even for the 546 nm band of the arc lamp, is be incurred as a consequence of using solid state light engine 630 as a replacement for an arc lamp.

As shown in FIG. 6B controller 652 is connected to each of the LED light sources 644 and light pipe engine 642. In a preferred embodiment, control of all of LED light sources 644 and light pipe engine 642 is ganged. For example, each of the LED light sources 644 and light pipe engine 642 is turned on and off at the same time and the power of each of the LED light sources 644 and light pipe engine 642 is modulated in the same way. Thus if one LED light source is dimmed by 50% all of the LED light sources 644 and light pipe engine are dimmed by 50%. To put it another way, as the light output of the preferred embodiment is desired to be white light, the LED light sources 644 and light pipe engine cannot be independently turned off an on or independently adjusted in power output. To the extent that a user desires to alter the spectral content of the white light, the user is required to modulate the white light with filters placed in the white light beam 648. Typically this is done using external bandpass filters in filter system 620.

Controller 652 communicates with software, cameras, microscopes, remote controls, and/or foot pedals to allow control of solid state light engine 630. For example in a preferred embodiment UNIBLITZ® command control is supported for on/off synchronization in place of an electronic shutter. For additional example, a remote control accessory can be used to facilitate control by allowing user operation without a dedicated computer or third party software. A remote control accessory can be compatible with 3rd party software control of the illuminator but simplifies light engine operation and reduces start up time. A camera interface provides exact synchronization in a complete imaging system. The camera interface to controller 652 eliminates lag time, minimizes photo-damage to sensitive samples, and ensures exposure of biological samples to only the required amount of light needed for a given experiment.

Because solid state light sources are used, the light engine can be turned on and off at a high switching speed not possible with arc lamps. For example, in an embodiment, the switching speed can be up to 5 kHz with turn on/off in approximately 10 μs. The high switching speed enable light blanking during frame readout thereby minimizing photo-bleaching during sample illumination and prolonging sample life. The short warm-up time of the system and superior stability of the solid state light sources provide for highly reproducible output power as well as a long expected lifetime greater than 15,000 hours without the need for arc lamp alignment, installation and replacement. Moreover, the solid state light engine also produces less heat, thus reducing the power and cooling requirements of the system as compared to arc lamp systems.

FIG. 6C is a graph showing spectral power of the solid state light engine of FIG. 6B in comparison to commonly used 120 W metal halide lamps and a 175 W Xenon lamps. As shown in FIG. 6C, the solid state light engine 630 generates white light which is continuous in the visible spectrum from 380 nm to 650 nm and is suitable for imaging all the most common fluorophores and fluorescent proteins. Advantageously, the spectral power of the solid state illumination system 600 is equal to or greater than the spectral power of a 120 W metal halide lamp or 150 W Xenon lamp across substantially the entire visible spectrum from 380 nm to 650 nm. In particular embodiments the spectral power is greater than 1 mW/nm over the substantially the entire visible spectrum from 380 nm to 650 nm and greater than 3 mW/nm over the range from 500-600 nm. The continuous white light provided solid state light engine 630 provides white light having a high color rendering index. Moreover, the color temperature, and other attributes of the white light can readily be modulated with external filters in filter system 120. Thus solid state light engine 630 can serve as a direct replacement for 120 W metal halide lamp or 150 W Xenon lamps.

In alternative embodiments, controller 652 can be designed to control LED light sources 644 and light pipe engine 642 individually (on/off and intensity) such that the spectral content of the output light can be modulated and/or changed in color. Moreover, in an alternative embodiment, filter system 620 can be integrated into housing 631 such that filters 622 can be inserted into the output light path manually (for example through a slot in the housing) or under the control of controller 652 (for example a motorized-controlled filter wheel).

The foregoing description of the various embodiments of the present invention has been provided for the purposes of illustration and description. It is not intended to be exhaustive or to limit the invention to the precise forms disclosed. Many modifications and variations will be apparent to the practitioner skilled in the art. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

The illuminations systems and components thereof described herein may, with suitable adaptation, find application in a range of applications including: life science applications which cover a range of white light and/or fluorescence analyses and quantitation; microscopy; fluorescence microscopy; high content screening; genetic expression analysis; digital pathology; and endoscopy.

Other features, aspects and objects of the invention can be obtained from a review of the figures and the claims. It is to be understood that other embodiments of the invention can be developed and fall within the spirit and scope of the invention and claims.

What is claimed is:

1. An illumination system, comprising:
    a first light source comprising a first LED which emits violet light and a first collimator which receives the violet light and emits a collimated beam of violet light;
    a second light source comprising a second LED which emits blue light and a second collimator which receives the blue light and emits a collimated beam of blue light;
    a third light source comprising a third LED which emits cyan light and a third collimator which receives the cyan light and emits a collimated beam of cyan light;
    a fourth light source comprising a fourth LED which emits red/orange light and a fourth collimator which receives the red/orange light and emits a collimated beam of red/orange light;
    a fifth light source comprising a plurality of LEDs which emit blue light, a luminescent rod positioned to receive the blue light, wherein the blue light is absorbed by the luminescent rod which then emits green light, and a fifth collimator which receives the green light and emits a collimated beam of green light;
    a controller configured to operate all of the first, second, third, fourth and fifth light sources simultaneously such that the collimated beams of violet light, blue light, cyan light, red/orange light, and green light are emitted simultaneously; and
    a plurality of dichroic mirrors which combine the collimated beams of violet light, blue light, cyan light, red/orange light, and green light to create a beam of white light which is directed at an input aperture of a light guide;
    wherein the white light is substantially continuous in the visible spectrum from 380 nm to 650 nm and has a spectral power which substantially equals or exceeds a usable spectral power of a 120 W metal halide lamp at substantially every visible wavelength between 380 nm and 650 nm.

2. The illumination system of claim 1, wherein said white light has a spectral power which substantially equals or exceeds a spectral power of a 150 W Xenon lamp over substantially all of a power of the visible spectrum from 380 nm to 650 nm.

3. The illumination system of claim 1, wherein said white light has a spectral power greater than 1 mW/nm at substantially every visible wavelength between 380 nm and 650 nm.

4. The illumination system of claim 3, wherein said white light has a spectral power greater than 3 mW/nm at substantially every visible wavelength between 500 nm and 600 nm.

5. The illumination system of claim 1, further comprising a filter system including a light filter positioned in the path of the white light to modulate the spectral content of the white light.

6. The illumination system of claim 1, wherein the first, second, third, fourth and fifth light sources are ganged such that all of the first second, third, fourth and fifth light sources are turned on and off together.

7. The illumination system of claim 1, wherein the first, second, third, fourth and fifth light sources are ganged such that the first second, third, fourth and fifth light sources cannot be independently controlled.

8. The illumination system of claim 1, wherein the plurality of LEDs of the fifth light source comprise at least one array of forty blue LEDs.

9. The illumination system of claim 1, further comprising a filter system and a liquid light guide for providing the white light to a microscope system.

10. The illumination system of claim 1 further comprising:
   a downstream filter system through which said white light is passed; and
   said downstream filter system capable of using one of a plurality of filters to modulate the white light.

11. The illumination system of claim 1 further comprising a liquid light guide through said white light is passed; and
   a downstream filter system through which the light exiting from the liquid light guide is passed.

12. An illumination system, comprising:
   a first light source comprising a first LED which emits violet light and a first collimator which receives the violet light and emits a collimated beam of violet light;
   a second light source comprising a second LED which emits blue light and a second collimator which receives the blue light and emits a collimated beam of blue light;
   a third light source comprising a third LED which emits cyan light and a third collimator which receives the cyan light and emits a collimated beam of cyan light;
   a fourth light source comprising a fourth LED which emits red/orange light and a fourth collimator which receives the red/orange light and emits a collimated beam of red/orange light;
   a fifth light source comprising a plurality of LEDs which emit blue light, a luminescent rod positioned to receive the blue light, wherein the blue light is absorbed by the luminescent rod which then emits green light, and a fifth collimator which receives the green light and emits a collimated beam of green light;
   a controller configured to operate the first, second, third, fourth, and fifth light sources simultaneously such that the collimated beams of violet, blue, cyan, red/orange and green light are emitted simultaneously; and
   an optical system comprising a plurality of dichroic mirrors which combines the collimated beams of violet, blue, cyan, red/orange and green light to create white light and directs said white light into a light guide;
   wherein the white light is substantially continuous in the visible spectrum from 380 nm to 650 nm and has a spectral power greater than 1 mW/nm at substantially all of each visible wavelength between 380 nm and 650 nm and has a spectral power which substantially equals or exceeds a usable spectral power of a 120 W metal halide lamp at substantially every visible wavelength between 500 nm and 600 nm.

13. The illumination system of claim 12, wherein said white light has a spectral power which substantially equals or exceeds a spectral power of 120 W metal halide lamp at substantially every visible wavelength between 380 nm and 650 nm.

14. The illumination system of claim 12, wherein said white light has a spectral power which substantially equals or exceeds a spectral power of a 150 W Xenon lamp at substantially every visible wavelength between 380 nm and 650 nm.

15. The illumination system of claim 12, further comprising a filter system including a light filter positioned in the path of the white light to modulate the spectral content of the white light.

16. The illumination system of claim 12, wherein the first, second, third, fourth, and fifth light sources are ganged such that all of the first, second, third, fourth, and fifth light sources are turned on and off together.

17. The illumination system of claim 12, wherein the first, second, third, fourth, and fifth light sources are ganged such that the first, second, third, fourth, and fifth cannot be independently controlled.

18. The illumination system of claim 12, wherein the plurality of LEDs of the fifth light source comprise at least one array of forty blue LEDs.

19. The illumination system of claim 12, further comprising a filter system and a liquid light guide for providing the white light to a microscope system.

20. The illumination system of claim 12, wherein the luminescent rod emits green and yellow light between 500 nm and 600 nm.

21. The illumination system of claim 12 further comprising a filter system which is associated with said liquid light guide so that the light exiting from the liquid light guide is passed through said filter system.

22. An illumination system, comprising:
   a first light source comprising a first LED which emits violet light and a first collimator which receives the violet light and emits a collimated beam of violet light;
   a second light source comprising a second LED which emits blue light and a second collimator which receives the blue light and emits a collimated beam of blue light;
   a third light source comprising a third LED which emits cyan light and a third collimator which receives the cyan light and emits a collimated beam of cyan light;
   a fourth light source comprising a fourth LED which emits red/orange light and a fourth collimator which receives the red/orange light and emits a collimated beam of red/orange light;
   a fifth light source comprising a plurality of LEDs which emit blue light, a luminescent rod positioned to receive the blue light, wherein the blue light is absorbed by the luminescent rod which then emits green light, and a fifth collimator which receives the green light and emits a collimated beam of green light;
   a controller configured to operate all of the first, second, third, fourth and fifth light sources simultaneously such that the collimated beams of violet light, blue light, cyan light, red/orange light, and green light are emitted simultaneously; and
   a plurality of dichroic mirrors which combine the collimated beams of violet light, blue light, cyan light, red/orange light, and green light to create a beam of white light which is directed at an input aperture of a light guide;
   wherein the white light has a spectral power greater than 1 mW/nm at substantially every visible wavelength between 380 nm and 650 nm and has a spectral power greater than 3 mW/nm at every visible wavelength between 500 nm and 600 nm and has a spectral power which substantially equals or exceeds a usable spectral power of 120 W metal halide lamp at substantially every visible wavelength between 500 nm and 600 nm.

23. The illumination system of claim 22, wherein said white light has a spectral power which substantially equals or exceeds a spectral power of 120 W metal halide lamp at substantially every visible wavelength between 380 nm and 650 nm.

24. The illumination system of claim 22, wherein said white light has a spectral power which substantially equals or exceeds a spectral power of a 150 W Xenon lamp at substantially every visible wavelength between 380 nm and 650 nm.

25. The illumination system of claim 22, further comprising a filter system including a light filter positioned in the path of the white light to modulate spectral content of the white light.

26. The illumination system of claim 22, wherein the first, second, third, fourth, and fifth light sources are ganged such that all of the first, second, third, fourth, and fifth light sources are turned on and off together.

27. The illumination system of claim 22, wherein the plurality of LEDs of the fifth light source comprise at least one array of forty blue LEDs.

28. The illumination system of claim 22, further comprising a filter system and a liquid light guide for providing white light to a microscope system.

\* \* \* \* \*